US009588071B2

(12) United States Patent
Nyfors (10) Patent No.: US 9,588,071 B2
(45) Date of Patent: Mar. 7, 2017

(54) MULTIPHASE METER (71) Applicant: Roxar Flow Measurement AS, Bergen (NO)

(72) Inventor: Ebbe Gustaf Nyfors, Sandnes (NO)

(73) Assignee: ROXAR FLOW MEASUREMENT AS, Bergen (NO)

( * ) Notice: Subject to any disclaimer, the term of this patent is extended or adjusted under 35 U.S.C. 154(b) by 75 days.

(21) Appl. No.: 14/397,829

(22) PCT Filed: Apr. 29, 2013

(86) PCT No.: PCT/EP2013/058880
§ 371 (c)(1),
(2) Date: Oct. 29, 2014

(87) PCT Pub. No.: WO2013/164303
PCT Pub. Date: Nov. 7, 2013

(65) Prior Publication Data
US 2015/0115979 A1 Apr. 30, 2015

(30) Foreign Application Priority Data
Apr. 30, 2012 (NO) .................................. 20120502

(51) Int. Cl.
*G01N 22/00* (2006.01)
*G01N 27/02* (2006.01)
(Continued)

(52) U.S. Cl.
CPC ........... *G01N 27/023* (2013.01); *G01N 22/00* (2013.01); *G01N 33/0004* (2013.01);
(Continued)

(58) Field of Classification Search
CPC .. G01N 33/2823; G01N 22/00; G01N 27/023; G01N 33/18; G01N 33/0004; G01N 33/28; G01R 25/00
(Continued)

(56) References Cited

U.S. PATENT DOCUMENTS 5,103,181 A   4/1992   Gaisford
5,341,100 A   8/1994   Taylor
(Continued)

FOREIGN PATENT DOCUMENTS

NO    982538      12/1999
WO    99/63331    12/1999
(Continued)

OTHER PUBLICATIONS

Ebbe Gustaf Nyfors, "Cylindrical Microwave Resonator Sensors for Measuring Materials Under Flow", Report S243, May 2000, pp. 1-181.
(Continued)

*Primary Examiner* — Son Le
*Assistant Examiner* — Akm Zakaria
(74) *Attorney, Agent, or Firm* — Nixon & Vanderhye PC (57) ABSTRACT

A multiphase meter system including: transmitting and receiving antennas in the flow pipe, wherein the receiving antennas are at different distances from the transmitting antenna, and a control system configured to: apply an electromagnetic field to the transmitting antenna and receive signals from the receiving antenna induced in the fluid or the pipe by the transmission of the electromagnetic field; calculate a resonance quality of the signals received by at least one of the first and second receiver antennas; calculate composition or salinity of the fluid based on the resonance quality if the resonance quality is greater than a threshold value, and calculate composition or salinity of the fluid
(Continued)

based on a transmission time difference of the signals received from the first receiver antenna and the signals received by the second receiver antenna if the resonance quality is below the threshold value.

23 Claims, 2 Drawing Sheets (51) Int. Cl.
G01N 33/28 (2006.01)
G01N 33/18 (2006.01)
G01N 33/00 (2006.01)
G01R 25/00 (2006.01)

(52) U.S. Cl.
CPC ............ *G01N 33/18* (2013.01); *G01N 33/28* (2013.01); *G01N 33/2823* (2013.01); *G01R 25/00* (2013.01)

(58) Field of Classification Search
USPC ........................................ 324/633
See application file for complete search history.

(56) References Cited

U.S. PATENT DOCUMENTS

| | | | | |
|---|---|---|---|---|
| 5,793,216 A * | 8/1998 | Constant | ............... | G01F 1/663 324/639 |
| 5,859,615 A * | 1/1999 | Toland | ............... | H01Q 13/0208 343/753 |
| 6,826,964 B2 | 12/2004 | Nyfors | | |
| 6,915,707 B2 | 7/2005 | Nyfors et al. | | |
| 7,631,543 B2 | 12/2009 | Wee | | |
| 2007/0224692 A1* | 9/2007 | Agar | ............... | G01N 27/22 436/150 |
| 2008/0012577 A1* | 1/2008 | Potyrailo | ............... | G01D 9/005 324/633 |
| 2009/0088985 A1* | 4/2009 | Wee | ............... | G01F 1/66 702/30 |
| 2009/0295405 A1* | 12/2009 | Pommerenke | ....... | G01R 31/002 324/627 |
| 2010/0145636 A1* | 6/2010 | Nyfors | ............... | G01F 1/584 702/49 |
| 2010/0308974 A1* | 12/2010 | Rowland | ............... | A61B 5/0031 340/10.4 |
| 2011/0098938 A1* | 4/2011 | Huang | ............... | G01F 1/663 702/25 |
| 2011/0196625 A1* | 8/2011 | Sheila-Vadde | ........... | G01F 1/66 702/49 |
| 2011/0267074 A1* | 11/2011 | Xie | ............... | G01N 33/2823 324/629 |

FOREIGN PATENT DOCUMENTS

| | | |
|---|---|---|
| WO | 2005/057142 | 6/2005 |
| WO | 2007/018434 | 2/2007 |
| WO | 2008/085065 | 7/2008 |
| WO | 2010/115883 | 10/2010 |

OTHER PUBLICATIONS

Lund Bo et al., Application of Microwave Spectorscopy for the Detection of Water Fraction and Water Salinity in Water/Oil/Gas Pipe Flow, Journal of Non-Crystalline Solids 305 (2002), 345-353.
Ebbe Nyfors et al., "Measurement of Mixtures of Oil, Water, and Gas with Microwave Sensors. New Developments and Field Experience of the MFI MultiPhase, and WaterCut Meters of Roxar", XP-002402006, Proceedings of SPIE vol. 4129 (2000), pp. 12-21.
Sidsel Corneliussen et al, "Handbook of Multiphase Flow Metering", Revision 2, Mar. 2005, 116 pages.
Ebbe Nyfors et al., "Industrial Microwave Sensors", Artech House, 1989, 23 pages.
International Search Report cited in PCT/EP2013/058880 mailed Jul. 2, 2013.

* cited by examiner

MULTIPHASE METER

RELATED APPLICATIONS

This application is the U.S. national phase of International Application No. PCT/EP2013/058880 filed Apr. 29, 2013, which designated the U.S. and claims priority to Norwegian Patent Application 20120502 filed Apr. 30, 2012, the entire contents of each of these application are incorporated by reference.

BACKGROUND

The present invention relates to a multiphase meter system for measurements of composition and/or salinity of a fluid flow in a pipe.

More specifically the present invention relates to measurement of water, oil, gas and/or salinity fractions in a fluid flow in the exploration of oil and gas reservoirs.

A number of different commercial flow meters are available on the market for the measurement of the content of fluid flows from oil wells. Some meters are based on the use of radioactive radiation, some are capacitive, and some are based on the use of microwaves.

Microwave sensors are attractive because they are not limited by the health risks associated with radioactive radiation based meters and their fairly low accuracy or the undesirable influence of contamination on the capacitive sensors.

An example of a method for measuring properties of flowing fluids and a metering device and a sensor used for performing this method has been described in International Patent Application PCT/NO01/00200, for which a US-patent has been granted (U.S. Pat. No. 6,826,964 B2). The sensor uses the microwave resonance principle for the measurement of oil-continuous fluids (water drops and gas bubbles in oil, i.e. the oil is a continuous phase) and the measurement of conductivity for water-continuous fluids (oil drops and gas bubbles in water, i.e. the water is the continuous phase, and is intended for installation at a production zone inside an oil well. Another example of resonance measurements in multiphase flows is discussed in Norwegian patent 308922 (corresponding to WO99/63331).

Another example of a method for measuring flowing fluids with a far higher gas content, i.e. wet gas (a wet gas flow is a multiphase flow with a high gas volume fraction, usually called the gas void fraction (GVF), typically >99%) or high-gas multiphase flow, has been described in U.S. Pat. No. 6,915,707. This is also based on the microwave resonance principle.

The microwave resonance principle is based on measuring the permittivity/dielectric constant of the flow and is discussed with reference to water volume fractions (WVF) in WO 2008/085065.

Other systems are described in U.S. Pat. No. 5,101,163 and WO2007/018434, as well as U.S. Pat. No. 5,341,100, where the composition and water salinity is measured by measuring the difference in the signal received by two antennas being positioned at different distances from the transmitter antenna, called the transmission method. This method is usually preferred when the loss in the fluid flow is high, e.g. in a water continuous flow with relatively high water salinity.

A problem inherent in the known art is that it is difficult to provide sufficiently accurate measurements within the complete range of compositions and salinities within the same fluid volume. As is discussed above the resonant frequency and Q-factor is suitable for a certain range of fractions, but less suitable when the loss in the flow gets sufficiently high and the accuracy is reduced. This problem is solved as described in the claims.

SUMMARY OF THE INVENTION

Thus the present invention is related to a MUT (material under test) flowing in a metal pipe, where the dielectric properties of this MUT are to be measured by microwaves, e.g. for the purpose of finding the composition of the MUT, e.g. the mixture ratio between oil and water. The MUT may exhibit so-called high-loss or low-loss properties depending on e.g. whether the water or the oil is the continuous phase in the case of an oil/water mixture, and depending on whether the water contains dissolved ions, e.g. salts, making it more or less conductive. In "Handbook of Multiphase Flow Metering" fra 2005, ref [4] in *Microwave technology*, on page 51 and 52 it is stated on page 52, that a practical microwave MPFM uses the resonator principle for oil-continuous fluids, and the varying frequency transmission principle in water-continuous fluids, utilizing the same probes. When the attenuation is low, the pipe acts as a resonator and, when the attenuation is high, the phase difference between two receiving probes is detected. The solution described in [4] is based on the use of the pipe as resonator. Other examples are given in WO2005/057142 and U.S. Pat. No. 7,631,543. The resonator as such is not ideal as the main resonance occurs at the cutoff frequency and resonating energy will leak in the direction of the pipe, thus reducing the accuracy of the system. The present invention solves this problem by using a resonator having a resonance frequency below cutoff and thus a resonance peak being easily detected so as also to improve the performance in flow measurements.

For the measurement purpose a microwave resonator has been implemented in the pipe for measuring under low-loss conditions, and typically three antennas for performing differential transmission measurements under high-loss conditions. The reason for using both methods is that the resonator method is the most accurate method when the losses are low enough for this method to work, and the transmission method being best suited for high losses because it can be used in a wide dynamic range.

Besides the transmission method is less accurate under low-loss conditions due to the influence of wave modes and reflections. In a preferred embodiment the same antennas are used both for coupling to the resonator and for performing the transmission measurements, with the exception that only two of the antennas are used for the resonator measurement.

The frequency response, i.e. the transmission function as a function of frequency, measured between a transmitting antenna and a receiving antenna will display features of direct capacitive coupling, resonances, and direct transmission. Depending on the amount of losses some of these will dominate. Under low-loss conditions the resonance peak(s) will be clearly visible above a baseline of capacitive coupling. Under high-loss conditions no peaks will be visible. Neither will direct capacitive coupling be of any importance. Instead direct transmission will dominate and the measured phase shift and attenuation are related to the dielectric properties of the MUT and the propagated distance. By using differential transmission, i.e. comparing transmission between identical pairs of antennas with different propagation distance, the influence of the properties of the antennas and the rest of the system, including cables and connectors, are cancelled, displaying the true effect of the propagated distance through the MUT.

In the case of a two-phase mixture of oil and water, where the water contains some amount of dissolved ions, typically equivalent to more than 0.1% of NaCl, the mixture will display clearly low-loss or high-loss properties depending on whether the mixture is oil- or water-continuous. In this case the situation is easy to detect from the presence or absence of resonance peak(s), and the measurement method chosen accordingly. In other cases, e.g. if the water is more or less fresh (equivalent content of NaCl below 0.1%), or if significant amounts of gas are present, as in a 3-phase mixture of oil, water and gas with a high GVF (Gas Void Fraction), situations may appear, where the losses are neither high nor low. In this case the frequency response will display both resonance peaks, which have a low Q-factor, i.e. they look more like humps on the response than peaks, and transmission clearly above pure capacitive coupling. In this case it may not be immediately clear which method is preferable to use.

The best strategy in this case is to measure with both, and perform a quality check on the results before choosing which one to output as the measurement result. The quality check may contain e.g. criteria related to the expected range of the e.g. volume fractions, criteria related to the expected maximum speed of change of the volume fractions, and criteria related to the stability (variance) of the measurements with the two methods. To determine when both methods should be used in the above described way, or only resonance or differential transmission measurements, a set of characterizing constants can be used. These can e.g. be the Q-factor of the resonance peak(s) (if the peak(s) are not identifiable the case is a high-loss case), and the attenuation ratio at a hump (poor resonance peak) and the trough or valley above (in frequency) it. A limit can be that the Q-factor must be >10 for the resonance method to be used, and between "not identifiable" and 10 for both methods to be used. Similar criteria can be defined for the attenuation ratio, or a factor depending on both can be defined.

Which criteria to use are best found empirically by performing flow tests in practice, logging raw data, and then recalculating e.g. the composition by applying various limits and criteria.

For best results the sensor system with the resonator and the antennas should be designed so that only the resonance peak(s) to be used are within the frequency range to be used. In most cases this means that only one peak should influence the measured frequency response. The transmission measurement should also be designed so that the measurements of phase and/or attenuation are performed in a part of the frequency range least affected by the resonance as long as the peak has not disappeared completely due to high losses. The word "pin" is often used for the antennas, especially when implemented in a probe.

In the following specification the following definitions are applicable:

Frequency response: The coupling (attenuation and phase shift) from one antenna to another as a function of frequency. The coupling is called insertion loss.

Low-loss: The attenuation of the microwave energy fed into a pipe through a coupling antenna is so low that reflections from the pipe walls form an interference pattern in the form of wave-guide modes, or the coupling of energy from one antenna to another (the insertion loss) is dominated by direct capacitive coupling (in the case the frequency is lower that the lowest cut-off frequency of the waveguide modes in the pipe).

High-loss: The attenuation of microwaves in the medium is so high that propagating waves, which are reflected from the pipe walls and thereby travel a longer distance than those propagating from antenna to antenna, are attenuated so much that no influence of wave modes is detectable in the frequency response (insertion loss).

Thus a solution is obtained according to the invention where resonance is used in part of the measurements, but if the loss in the fluid rises a transmission method is applied by switching to measuring the phase difference and difference in measured damping in the flow. By simultaneously increasing the measuring frequency the salinity may also be measured.

According to the preferred embodiment of the invention the system comprises only three antennas, one transmitter and two receivers. When the resonance has a high quality only the transmitter and at least one of the receiver antennas are active. Thus the measurement is performed by transmitting a frequency sweep signal within a predetermined range and measuring both the resonance frequency and the width of the resonance peak, thus e.g. providing the Q-factor. If the quality of the resonance frequency is less than a predetermined value the phase and damping differences in the signals measured by the two receivers are found and used to characterize the composition of the flow. In this mode a different frequency range may be utilized so as to increase the accuracy of the measurements and also possibly to measure the salinity of the flow from the relationship between the real and imaginary parts of the signal, e.g. as described in U.S. Pat. No. 5,103,181, calculating the composition from the permittivity and the Brüggemann equation and in reference [2] Nyfors, E., P. Vainikainen, "Industrial Microwave Sensors", Artech House, 1989, 350 p, finding the permittivity from resonator and transmission measurements.

The system according to the present invention utilizes both resonance and transmission measurements, either by performing both types of methods simultaneously and choosing the most relevant information to be transmitted to the user, or by monitoring the quality of the measurements and shifting to the alternative measuring method if the measurements are below a certain threshold. The quality threshold of the resonance measurements may be defined by chosen values of Q-factor, peak width and/or resonance frequency while the quality threshold of the transmission measurements may be defined empirically, e.g. depending on the content of the fluid flow, sensor characteristics and pipe dimensions and materials.

SUMMARY OF THE DRAWINGS

The invention will be discussed below with reference to the accompanying drawings, illustrating the invention by way of examples.

DETAILED DESCRIPTIN OF EMBODIMENTS OF THE INVENTION

The invention is a further development of a wet gas meter (WGM) as described in U.S. Pat. No. 6,915,707, which has a microwave resonator sensor for measuring the permittivity of the flow for the calculation of the WVF (Water Volume Fraction). This works well at low WVF, but now the goal is to extend the operating range further down in GVF (up in WVF), where the flow becomes too lossy for the resonator to work well. The idea is to add a transmission type of measurement.

The known WGM described in WO 2008/085065 is based on a pure resonator measurement and therefore only works under low-loss conditions. It has two antennas and the electronics is only capable of measuring the amplitude of the insertion loss, i.e. the power attenuation, and only over a limited frequency range defined by the VCO(s) in the particular version of the unit used in the meter.

The main advantage of a sensor, where the whole pipe is the resonator, is that it is non-intrusive. But is has the serious weakness that the flow may obtain various flow regimes. E.g. the liquid may form a layer close to the pipe wall, while the gas passes in the middle. This is called annular flow. Such inhomogeneous distribution of the gas and liquid affect the measurement of the permittivity. Especially under water-continuous conditions and annular flow the measurements are in error. This is what has been tried to improve in WO2005/057142 and WO2007/018434 by adding another measurement, which weights the permittivity of the flow close to the wall, and then compensate for the known error using empirical models. The advantage with the WGM is that the flow is always squeezed through the gap between the pipe wall and the preferably conically shaped insert, which eliminates such flow regimes when the measurement is performed in this region. The current resonator measurement measures the flow in this gap around the whole circumference. The transmission measurement to be added must also be located so that the flow is measured roughly, when it passes the cone. At the same time the cone should preferably not affect the measurement, i.e. it should not be "seen" by the probes. It will not be possible to achieve measurement around the whole circumference, but assuming roughly symmetrical flow, this would not be necessary. As stated above the preferred embodiment utilizes a conically shaped insert, but other inserts may also be used such as a fin.

For a full 3 phase measurement (oil, water, gas) it will also be necessary to add a densitometer. Because there are 3 unknowns, one needs three equations to be able to solve composition. Two equations are related to the measurement of the permittivity and the density, and the third states that the sum of all three components equals to 100%. The present invention is mainly related to a means for providing the permittivity measurements while other calculations may be performed as in general Multi Phase Meters.

The idea according to the invention involves the addition of a transmission measurement, for example by transmitting with one probe acting as a transmitting antenna and receiving with two probes acting as receiving antennas. The two receiving probes must be at different distance from the transmitting probe. The difference in distance results in a phase difference. The frequency, where the phase difference obtains a predefined fixed value is measured. As will be seen the receiving and transmitting probes may be exchanged with one probe having three antennas acting as receiving or transmitting antennas.

The present invention relates to an optimized use of two measuring principles wherein the resonance is measured while also monitoring the quality of the resonance. The quality conditions of the resonance may be related to the width and symmetry of the peak. By roughly finding the resonant frequency and the 3 dB points (i.e. the half-power points, which are normally used for measuring the peak width for the Q-factor) directly from the peak, one can calculate the Q-factor (the resonant frequency divided by the peak width) and the asymmetry (e.g. relative difference between the measured resonant frequency and the mean of the 3 dB points). A more accurate method is related to a high-accuracy method of measuring the resonant frequency and the Q-factor. Then first a number of samples are measured in the range around the peak. Then the samples above the 3 dB level are used and the theoretical resonance curve (Eq. (3.27) in [3]) is fitted to them. This gives an accurate value for both the resonant frequency and the Q-factor. The asymmetry can be calculated using various methods by comparing the samples with the resulting curve. One method can be e.g. to calculate the mean deviation between the samples and the curve on both sides of the resonant frequency. When the Q-factor is less than e.g. 10, the resonance peak is difficult to measure, and indeed identify from other variations in the response. A limit for the asymmetry must be established based on empirical testing and comparing to results using both the resonator method and the transmission method. At the chosen limits, depending on the conditions in the pipe, the system may then change to measure differential transmission (phase and/or attenuation) between the antennas. The transmission conditions need to be determined for each case as the transition measurements may be affected by resonances and reflections in the pipe. Some empirical testing may be needed for a specific sensor design and application also because the local flow conditions at the antennas may be affected by these factors.

The resonance and transmission measurements may be performed within the same range of frequencies, but as the transmission signal will be affected by reflections and resonances in the range of conditions, where these two methods overlap, these frequencies should be avoided. In practice the resonance frequencies may be within the range of 100-2500 MHz depending on e.g. the physical size, but typically wet gas measurements using MDP cones, e.g. of the types discussed in WO2010/115883, are performed in the range of 400-1500 MHz.

Salinity measurements, e.g. as discussed in reference [1] may typically require transmission measurements in the range of 1-3 GHz, but for other transmission measurements lower frequencies down to a few tenths of MHz may be used.

It is, however, an advantage of the present invention that the system may adapt to the optimal frequency range for each of the measurements.

Below different embodiments and combinations of probes are discussed for performing the measurements according to the invention. The probes and the methods for using resonance and transmission measurements are considered to be part of the known art, e.g. as described in the referred articles and patent publications and will not be discussed per se in this specification.

Embodiment 1: Adding a Third Probe

Figure 1:
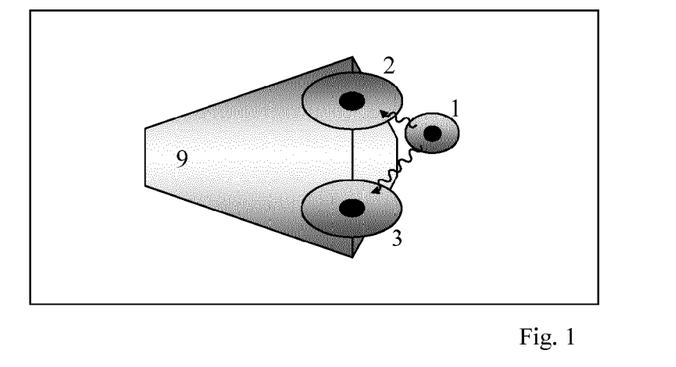
FIG. 1 Sketch of a first embodiment of the invention providing a third probe downstream of a two probe system for resonator measurements, and using that for transmission to avoid transmission along the rim of the cone.

Referring to FIG. 1 the known WGMs have two probes, each having one antenna 2,3, while the transmission type of measurement needs three probes. By adding a third probe with a third antenna 1, both types of measurements can be performed. The third probe could be smaller than the others, because the other two have been dimensioned to give optimal coupling to the resonator.

The two existing probes are located in the pipe wall exactly opposite to the widest part of a cone 9. One may therefore assume that the proximity of the cone will affect the transmission measurement. There may then be an effect, which depends on the β-value, which is related to the size of the cone relative to the pipe. This is undesirable as it makes calibration more complicated. By locating the third probe 1 further downstream asymmetrically in respect to the other two 2,3, and using this probe 1 for transmission, the influence of the cone could be reduced.

Advantages with this embodiment are:
  A total of only three probes.
  All probes are identical, or at least of similar type.
Disadvantages are:
  Needs switches to be able to change which is the transmitting probe.
  Two of the probes are large in diameter. Hence the distances between the probes will be large, meaning high maximum attenuation, and different flow conditions at the location of the third probe. Higher attenuation means that the maximum WVF the meter can handle is reduced compared to having shorter propagation distances, if the sensitivity of the electronics is a limiting factor.
  If possible, it would be desirable to mount the two existing probes closer to each other than normally. This would increase the direct coupling, which may affect the highest losses for which the resonator method can be used.

Embodiment 2: Adding a Probe with 3 Antennas

Figure 2:
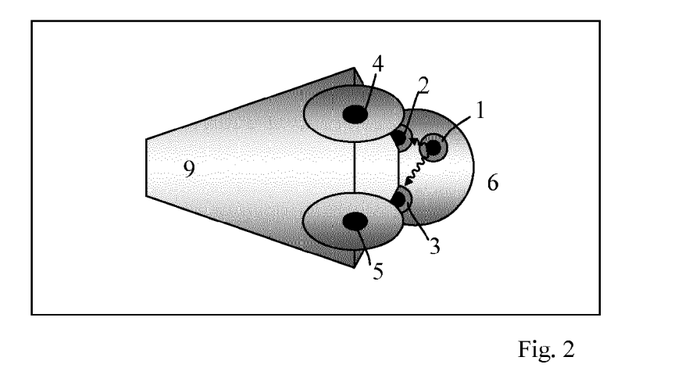
FIG. 2 Sketch of a second embodiment of the invention using a 3-antenna probe for transmission measurements, and maintaining the 2 standard probes for resonator measurements.

Referring to FIG. 2 a 3-antenna probe 6 has been developed for performing a 2-parameter measurement either as a stand-alone unit, or in a multiphase meter to find the salinity in the water. The idea was to measure both the phase and the attenuation at a high enough frequency (3 GHz suggested) that also the real part of the permittivity affects the measurements. Because the imaginary part caused by the conductivity is inversely proportional to the frequency, the imaginary part totally dominates over the real part at low frequencies. A paper on the sensor has been published, see reference [1]. The development involved theoretical studies, building of simple prototypes to study the optimal spacing and length of the antennas, and finally production of glass-moulded "final" probes.

Abovementioned U.S. Pat. No. 7,631,543 and WO2007/018434 describes a way of performing a 2-parameter measurement with the same type of 3-antenna 1,2,3 unit 6, which is based on measuring the phase only, but at two frequencies. This, and other alternative ways of performing multi-parameter microwave measurements, have also been described in [2]. In [2] a measurement is described measuring e.g. the phase at two frequencies as an alternative to measuring the attenuation and phase at one frequency.

The concept of using a 3-antenna probe for performing 1-parameter transmission measurements in the WGM would mean that the probe must be mounted close to the cone to achieve the advantage of eliminating the effect of flow regimes. On the other hand the measurement should not be directly affected by the proximity of the metal cone. It would appear that the optimal place to mount the probe would be right after the cone, as depicted in FIG. 2, which also illustrates the resonance measuring antennas 4,5 close to the cone.

Advantages with this concept are:
  The resonator measurement is not affected in any way.
  The 3-antenna probe can be standardized for each pipe size.
Disadvantages are:
  Needs even more switches than the concept with only 3 probes.

Embodiment 3: Using Only a 3-Antenna Probe

Figure 3:
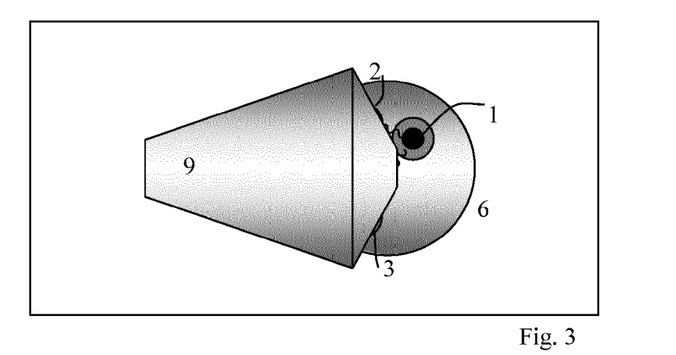
FIG. 3 Sketch of a third embodiment of the invention a 3-antenna probe.

The concept shown in FIG. 3 is a combination of the two previous concepts. Instead of having three separate probes as in the first concept, they would be integrated into one single probe 6 housing containing three antennas 1,2,3. To provide enough coupling for the resonator measurement, the probe antennas would probably need to be made larger than in the 3-antenna probe in the second concept. They would probably also need to be further away from each other to limit the direct capacitive coupling. The design would probably need to be different for each β-ratio.

The current probes, which are designed considering the resonator measurements only, are designed to always give roughly the same coupling in an air-filled meter, which gives a signal level close to the maximum in the dynamic range of the electronics. A lower signal level may be accepted, provided it will always stay above the noise level.

The probe must be located so that two of the antennas are roughly opposite to the rim of the cone. However, based on previous simulations it is clear that they could be displaced some millimeters in the direction of the third probe, which would reduce the influence of the cone on the transmission measurement.

The three probes in the housing do not necessarily have to be of the same size. The transmitting probe (downstream) could well be somewhat smaller.

Advantages with this concept are:
  There would only be one probe housing, and only one hole in the meter body.
  The 3 antennas can be more closely spaced than with three separate probes.
Disadvantages are:
  The probes for the resonator measurement are affected. It must probably be accepted that the signal level (peak height in the resonator) will be lower than in the current design, and vary with meter size and β-ratio. The direct capacitive coupling will also be higher.
  The existing 3-antenna design cannot be used directly but needs to be developed further.

Embodiment 4: Adding a 2-Antenna Probe

Figure 4:
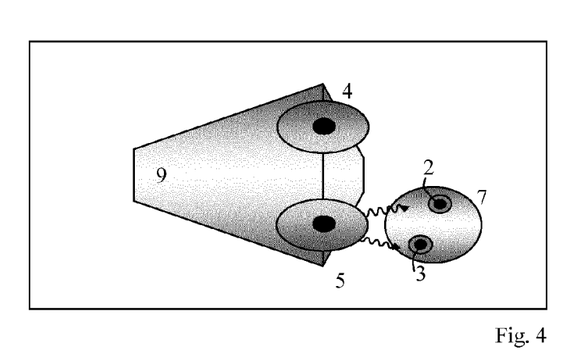
FIG. 4 A sketch of a fourth embodiment of the invention adding a 2-antenna probe.

In the concept shown in FIG. 4 the two current probes 1,5 would be used for the resonator measurement as before. In addition there would be a 2-antenna 2,3 probe 7 in the vicinity of the current transmitting probe 1. For transmission measurements one would switch to receive with the 2-antenna probe. One channel can be connected to one of the antennas permanently.

Advantages with this concept are:
  The resonator measurement is not affected in any way.
  The 2-antenna probe can be standardized for each pipe size.
Disadvantages are:
  The achievable path length is limited.

Embodiment 5: Replacing One Probe with a 3-Antenna Probe

Figure 5:
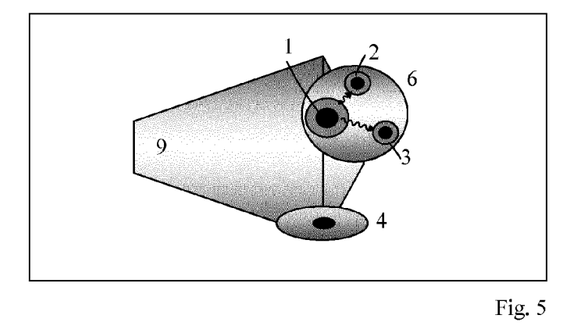
FIG. 5 A sketch of a fifth embodiment of the invention replacing one probe with a 3-antenna probe in a two probe resonance measuring system.

If one of the standard probes is replaced by a 3-antenna 1,2,3 probe 6 in such a way that one antenna 1 replaces the standard probe 5, and the two others 2,3 are downstream, the distance between the resonator probes can be maintained, while the transmission distances are kept short, and there are only two holes. The transmitting antenna can be larger than the others. The concept is depicted in FIG. 5.

Advantages with this concept are:
  The distance between the resonator probes can be maintained.
  Only two holes needed in the meter body.
  The 3-antenna probe can be standardized for each pipe size.
  Needs only one switch. The transmitting probe can always be the same.
  Because one resonator probe is as before, the necessary drop in peak level is smaller than in concept 3.

Disadvantages are:
  Unsymmetrical coupling. Therefore lower Q-factor than achievable for a given peak height.

The size of the standard probes for the resonator, e.g. in embodiments 1 and 4 may affect their use. Embodiment 2 would provide the highest degree of freedom in designing the transmission measurement, but involves the highest amount of switches. Embodiment 3 seems to be preferable as it only requires one hole for probes in the meter body, and a minimum amount of switches, and it allows shorter distances between the probes (than embodiments 1 and 4) giving lower attenuation and more uniform flow conditions, but it affects the coupling to the resonator. Compared to embodiment 3, embodiment 5 maintains the distance between the resonator probes, results in smaller reduction in signal level in the resonator, but requires 2 holes in the meter body.

A number of considerations may be made when choosing the probe embodiment for finding the optimal design under the specific use, such as:
  The influence of the cone, such as proximity, size and the requirements related to transmission length.
  Probe size and how closely spaced the probes can be from a mechanical point of view.
  The probe antennas, especially if there is more than one in each probe, may be designed to be both robust and tolerate some erosion, and to fulfill the criteria from a measurement point of view. The distance between the antennas may also be studied depending on the application of the invention.
  The maximum attenuation in the used frequency range needs to be evaluated based on the transmission length, path difference, and defined worst case conditions, and compared to the performance of the applied electronics.
  The flow conditions such as emulsions or flowing or bubbling water with varying salinity.
  The range of the variations in the signal strength, and the dynamic range of the electronics must be considered with respect to the required coupling of the resonator.

Embodiment 6: A Fin Type Insert

Figure 6A:
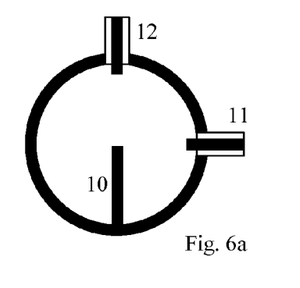
FIG. 6 illustrates an embodiment combined with a fin sensor.
Figure 6B:
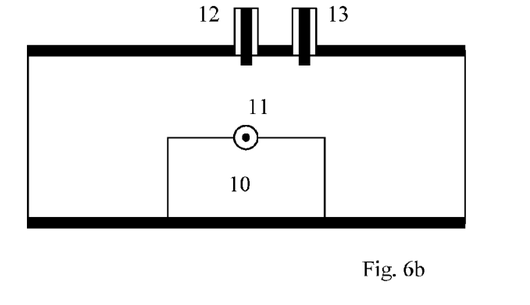

In FIG. 6a and 6b a measuring system according to the invention is positioned in a pipe with a fin type insert 10. Three antennas 11,12,13 have been positioned in the pipe wall, where FIG. 6a shows the position of two antennas 11,12 in the same axial position and a third antenna 13 at a distance downstream from the others. If the first antenna 11 is used as a transmitter there will be a difference in the propagation length from the first antenna 11 to the other antennas 12,13, which may be used in the transmission mode measurements.

The meter system according to the invention may advantageously be combined with other resonators, thus a combination of differential pressure measurements, microwave resonance and differential microwave transmission measurements e.g. to provide an addition to the invention described in U.S. Pat. No. 6,915,707 to comprise three probes enabling differential transmission measurements. One example might be a fin sensor in a venture, as illustrated in FIG. 5 in the patent, a solution without a venture or other differential pressure measurements may also be contemplated to make a two phase meter measureing the ratio between water and oil in a 0-100% mixture, as is illustrated in the present FIG. 6.

Thus to summarize the present invention relates to a multiphase meter system for measurements composition and/or salinity of a fluid flow in a pipe. The meter system comprises a resonance measuring means including a transmitting antenna for providing varying electromagnetic field within a first frequency range in the pipe and a receiver antenna for measuring the resonance characteristics of the field in said pipe and an evaluation means for determining the quality of said resonance.

The system also comprises a transmission measuring means including a transmitting antenna for transmitting a varying electromagnetic signal within a second frequency range, at least two receiver antennas being positioned at different distances from said transmitter antenna, and a time measuring means for determining the phase difference and difference in measured damping between the receipt of the transmitted signal at said two receiver antennas. The transmission and resonance measuring means being positioned so as to provide measurements in essentially the same fluid volume. This may preferably be obtained by using the same antennas or probes for both measurements.

The system according to the invention includes control means for comparing the resonance quality with a predetermined threshold value and when said resonance quality is above said threshold calculating the composition and/or salinity from said resonance characteristics or when said resonance quality is below said threshold calculating said composition and/or salinity from said transmission time difference and loss. Thus the most accurate measurements may be used depending on the content and characteristics of the fluid flow.

The quality of the resonance and the corresponding threshold is preferably calculated as the Q-factor of the resonance peek, thus indicating the loss in the resonator.

The transmitting antenna of the resonance measuring means and the transmission measuring means may be constituted by the same antenna, and possibly the receiver antenna of said resonance measuring means is constituted by one of receiver antennas of the transmission measuring means, using a limited number of antennas and intrusions through the pipe wall.

The first and second frequency ranges may be at least partially overlapping but preferably includes the optimal range for each measurement. The transmitted signals may thus be constituted by a broad band of frequencies corresponding to the first and second frequency ranges, while the receivers may be able to recived the complete range or the ranges for either resonance or transmission measurements. Preferably the first frequency range used for resonance measurements may be in the range of 100-2500 MHz, preferably within 400-1500 MHz, while the second frequency range for transmission measurements may be in the range of 400-3000 GHz, preferably 1000-3000 MHz.

The salinity of the fluid in the flow may also be calculated as a function of the real and imaginary values measured by the transmission measuring means.

The resonance measuring means and said transmission measuring means are preferably operated essentially simultaneously, as the control means is adapted to compare the quality of the measurements from the measuring means and provide an output indicating the measurements having the highest quality. Alternatively the output may be based on said measurements being weighted according to the calculated quality of the measurements. Thus a combined output signal may be provided being an optimized combination of said measurements.

While the antennas, and especially the resonance measuring antennas, preferably are mounted close to an insert, such as a cone or fin, having an axial position in a pipe, other situations may also be contemplated. Used close to a cone the resonance measurements should preferably be performed close to the widest brim of said cone.

REFERENCES

[1] Bø, Ø. L., E. Nyfors, "Application of microwave spectroscopy for the detection of water fraction and water salinity in water/oil/gas pipe flow", *J. of Non-Crystalline Solids* (Elsevier), 305, 2002, pp. 345-353. (Also presented *Dielectric Spectroscopy*, Jerusalem January 2001).
[2] Nyfors, E., P. Vainikainen, "*Industrial Microwave Sensors*", Artech House, 1989, 350 p.
[3] Nyfors, E., *Cylindrical Microwave Resonator Sensors for Measuring Materials under Flow*, Thesis, Helsinki Univ. of Tech., Radio laboratory, Report S 243, 2000, 181 p.
[4] Nyfors et al: Handbook of Multiphase Flow Metering, page 51-52.

The invention claimed is:

1. A multiphase meter system for measurements of composition and/or salinity of a fluid flow in a pipe, the system comprising:
 a resonance measuring system including a transmitting antenna for providing varying electromagnetic field within a first frequency range in the pipe and a receiver antenna for measuring the resonance characteristics of the field in said pipe,
 a transmission measuring system including a transmitting antenna for transmitting a varying electromagnetic signal within a second frequency range, at least two receiver antennas being positioned at different distances from said transmitter antenna,
 said transmission and resonance measuring systems being positioned so as to provide measurements in essentially the same fluid volume, and
 a controller configured to:
  determine the quality of said resonance based on the measured resonance characteristics of the field in said pipe;
  determine the phase difference and difference in measured damping between the receipt of the transmitted signal at said two receiver antennas of the transmission measuring system;
  compare a resonance quality with a predetermined threshold value;
  when said resonance quality is above said threshold, calculate the composition and/or salinity from said resonance characteristics; and
  when said resonance quality is below said threshold, calculate said composition and/or salinity from said transmission phase difference and damping.

2. The multiphase meter according to claim 1, wherein the quality of the resonance and the corresponding threshold is represented by a Q-factor of the resonance peak.

3. The multiphase meter according to claim 1, wherein the transmitting antenna of the resonance measuring system and the transmission measuring system is constituted by the same antenna.

4. The multiphase meter according to claim 3, wherein the receiver antenna of said resonance measuring system is constituted by one of the receiver antennas of the transmission measuring system.

5. The multiphase meter according to claim 1, wherein said first and second frequency ranges are at least partially overlapping.

6. The multiphase meter according to claim 1, wherein the transmitted signals are constituted by a broad band of frequencies corresponding to the first and second frequency ranges.

7. The multiphase meter according to claim 1, wherein said first frequency range is in the range of 100-2500MHz.

8. The multiphase meter according to claim 1, wherein second frequency range is in the range of 400-3000GHz.

9. The multiphase meter according to claim 8, wherein the salinity of the flow is calculated as a function of phase and damping values measured by the transmission measuring system.

10. The multiphase meter according to claim 1, wherein said resonance measuring system and said transmission measuring system are operated essentially simultaneously.

11. The multiphase meter according to claim 1, wherein said resonance measuring system and said transmission measuring system are operated essentially simultaneously, said controller is configured to compare the quality of the measurements therefrom and calculate an output based on said measurements being weighted according to a calculated quality of the measurements.

12. The multiphase meter according to claim 1, wherein said resonance measuring system is positioned close to an insert in the pipe.

13. The multiphase meter according to claim 12, wherein the insert has a conical shape, and the resonance measuring system is positioned close to a widest brim of said cone.

14. The multiphase meter according to claim 12, wherein the resonance measuring system includes the insert, the resonance being provided between said antennas and the insert.

15. A multiphase meter system configured to be positioned on a flow pipe for a fluid, the system comprising:
 a transmitting antenna positioned in the flow pipe;
 a first receiver antenna positioned in the flow pipe at a first distance from the transmitting antenna;
 a second receiver antenna positioned in the flow pipe positioned in the flow pipe at a second distance from the transmitting antenna, wherein the second distance is different than he first distance;
 a control system including a source of an electromagnetic field having a variable frequency, wherein the control system is configured to apply the electromagnetic field to the transmitting antenna and to receive signals from each of the first and second receiver antennas due to the transmitted electromagnetic field, and further wherein the control system is configured to:
  calculate a resonance quality of the signals received by at least one of the first and second receiver antennas;

calculate composition or salinity of the fluid based on the resonance quality if the resonance quality is greater than a threshold value; and calculate composition or salinity of the fluid based on a transmission time difference of signals received from the first receiver antenna and signals received by the second receiver antenna if the resonance quality is below the threshold value.

16. The multiphase meter system of claim 15 further comprising an insert having at least a partially conical shape and positioned in the flow pipe, wherein the transmission antenna and the first receiver antenna are aligned with a widest portion of the insert.

17. A method of measuring the composition or salinity of a fluid flowing through a pipe using a multiphase meter including a transmitting antenna and first and second receiving antennas, wherein the first and second receiving antennas are at different distances from the transmitting antenna, the method comprising:

transmitting from transmitting antenna an electromagnetic field having a frequency in a first frequency range into the fluid flowing through the pipe;

receiving at the first receiving antenna signals due to the transmission of the field having the first frequency, and using the received signals to calculate a resonance quality of the received signals;

calculating composition or salinity of the fluid based on the resonance quality if the resonance quality is greater than a threshold value;

transmitting from the transmitting antenna an electromagnetic field having a frequency in a second frequency range into the fluid flowing through the pipe, and if the resonance quality is below the threshold value, receiving at the first and second receiving antennas signals due to the transmission of the field having the second frequency, and using the received signals to calculate a composition or salinity of the fluid based on a damping difference of the signals received from the first receiver antenna and the signals received by the second receiver antenna.

18. The method of claim 17 wherein the first frequency range is 100 to 2500 MHz and the second frequency range is 400 to 3000 GHz.

19. The method of claim 17 further comprising positioning an insert having at least a partially conical shape in the flow pipe, wherein the transmission antenna and the first receiver antenna are aligned with a widest portion of the insert.

20. The method of claim 17 further comprising positioning a fin in the pipe and in the fluid flow, wherein the transmitting antenna and the first receiving antenna are aligned in the direction of fluid flow with each other and the fin.

21. The multiphase meter according to claim 2, wherein the Q-factor threshold value is close to 10.

22. The method of claim 17, wherein the resonance quality is determined using Q-factor of the resonance peak and the threshold value is close to 10.

23. The multiphase meter according to claim 1, wherein said resonance measuring system is positioned adjacent to a conical shaped insert inside of the pipe.

* * * * *